United States Patent [19]
Hancock et al.

[11] Patent Number: 6,063,811
[45] Date of Patent: May 16, 2000

[54] COMPOSITIONS FOR A ONCE DAY TREATMENT OF CYCLOOXYGENASE-2 MEDIATED DISEASES

[75] Inventors: Bruno Hancock, Beaconsfield; Conrad Winters, L'Ile Bizard, both of Canada; Barry Gertz, Summit; Elliot Ehrich, Chatham, both of N.J.

[73] Assignees: Merck & Co., Inc., Rahway, N.J.; Merch Frosst Canada & Co., Kirkland, Canada

[21] Appl. No.: 09/180,647

[22] PCT Filed: May 13, 1997

[86] PCT No.: PCT/US97/08041

§ 371 Date: Mar. 8, 1999

§ 102(e) Date: Mar. 8, 1999

[87] PCT Pub. No.: WO97/44028

PCT Pub. Date: Nov. 27, 1997

Related U.S. Application Data

[63] Continuation of application No. 08/851,756, May 6, 1997, abandoned
[60] Provisional application No. 60/017,878, May 17, 1996.

[30] Foreign Application Priority Data

Jun. 10, 1996 [GB] United Kingdom .................. 9612063

[51] Int. Cl.⁷ .................................................. A61K 31/34
[52] U.S. Cl. ............................................................ 514/473
[58] Field of Search .............................................. 514/473

[56] References Cited

U.S. PATENT DOCUMENTS 5,474,995 12/1995 Ducharme et al. .

FOREIGN PATENT DOCUMENTS

WO 95/00501 1/1995 WIPO .
WO 95/18799 7/1995 WIPO .

OTHER PUBLICATIONS

Clinical Pharmacology, Mar. 30, 1999, (3) 211–231, Thierry Lave, et al.
Journal of Pharmaceutical Sciences, vol. 86, No. 5, May 1997 p p 584–590.
Journal of Pharmacology and Experimental Therapuetics, vol. 283, No. 1, pp 46–58 (1997).
Davies, B. and Morris, T., Pharmaceutical Research 10, 1093–1095 (1993), T. Physiological Parameters in Laboratory Animals and Humans.
Lin, Drug Metabolism and Disposition, vol. 23, No. 10, 1008–1021 (1995).
Iwatsubo, et al., Biopharmaceutics & Drug Disposition, vol. 17, 273–310 (1996).
Mordenti, J., Journal of Pharmaceutical Science 75, 1028–1040 (1986), Man versus Beast: Pharmacokinetic Scaling in Mammals.
Rowland and Tozer, Clinical Pharmacokinetics: Concepts and Applications (1980).
Osteoarthritis and Cartilage: vol. 5 (Suppl. A) May 1997.
Arthritis & Rheumatism, vol. 40, No. 9(Suppl.) Sep. 1997.

*Primary Examiner*—William R. A. Jarvis
*Attorney, Agent, or Firm*—Curtis C. Panzer; David L. Rose

[57] ABSTRACT

This application relates to a method of treating a disease susceptible to treatment with a non-steroidal anti-inflammatory drug by administering to a patient once daily an effective amount of 3-phenyl-4-(4-methylsulfonyl) phenyl)-2-(5H)-furanone.

8 Claims, No Drawings

COMPOSITIONS FOR A ONCE DAY TREATMENT OF CYCLOOXYGENASE-2 MEDIATED DISEASES

RELATED APPLICATION DATA

This is a National phase U.S. application of PCT/US97/08041, filed May 13, 1997, which claims priority from U.S. Provisional Application 60/017,878, filed May 17, 1996 and British application GB 9612063.9, filed Jun. 10, 1996.

This application is also a continuation of U.S. Ser. No. 08/851,756, filed May 6, 1997 now abandoned, which claims priority from U.S. Provisional application 60/017,878, filed May 17, 1996.

BACKGROUND OF THE INVENTION

This invention relates to pharmaceutical compositions for the treatment of cyclooxygenase-2 mediated diseases, mehe use of a compound in the manufacture of a medicament.

In particular, this invention relates to a pharmaceutical composition for the treatment of cyclooxygenase-2 mediated diseases, said composition being suitable for once a day administration, said composition comprising a cyclooxygenase-2 inhibiting characterized by high potency for the inhibition of cyclooxygenase-2, a long half-life and a high degree of specificity for inhibiting cyclooxygenase-2 in preference to cyclooxygenase-1. Such a compound is exemplified by 3-phenyl-4-(4-methylsulfonyl)phenyl)-2-(5H)-furanone,

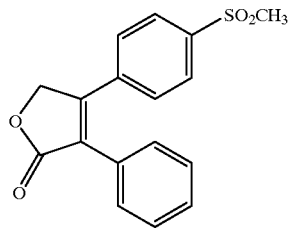

Non-steroidal anti-inflammatory agents are normally administered 2 to 4 times daily. The relatively short half-life of most non-steroidal anti-inflammatory agents means that once a day administration is impractical and even twice a day administration is unusual. The relatively large doses needed to achieve once a day treatment of conventional non-steroidal anti-inflammatory agents would also lead to side effects so that there is a general understanding that once a day administration is unlikely to be achievable.

Surprisingly a compound has been identified which can be employed on a once a day basis and which will not produce an unacceptable level of side effects on such a regimen, and in particular will not cause an unacceptable level of gastric side effects.

U.S. Pat. No. 5,474,995, issued Dec. 12, 1995, WO 95/00501, published Jan. 5, 1995 and WO 95/18799, published Jul. 13, 1995, disclose 3,4-di-substituted furanones and derivatives thereof as potent, selective inhibitors of cyclooxygenase-2. We have found that 3-phenyl-4-(4-methylsulfonyl)phenyl)-2-(5H)-furanone, possesses a surprising combination of attributes that make it possible to formulate and use the composition in a surprising manner. Not only is the compound potent, safe and effective at modest oral dosages of 5 to 125 mg of agent per day, but in addition this active agent possesses a half-life in humans of sufficient length that a single oral dose of 5 to 125 mg of agent per day will provide effective safe anti-inflammatory treatment over a 24 hour period. Such active agents are particularly useful in the treatment of chronic indications, including arthritis, pain, Alzheimer's disease and the like.

SUMMARY OF THE INVENTION

This invention is directed to a pharmaceutical composition for the treatment of cyclooxygenase-2 mediated diseases, said composition being suitable for once a day oral administration, said composition comprising a cyclooxygenase-2 inhibiting compound characterized by high potency for the inhibition of cyclooxygenase-2, a long half-life and a high degree of specificity for inhibiting cyclooxygenase-2 in preference to cyclooxygenase-1. Such a compound is exemplified by 3-phenyl-4-(4-methylsulfonyl)phenyl)-2-(5H)-furanone.

In one aspect, this invention is directed to a pharmaceutical composition for the treatment of cyclooxygenase-2 mediated diseases, aid composition being suitable for once a day oral administration, said composition comprising 5 to 125 mgs of the above mentioned compound.

The invention is also directed to a method of treating cyclooxygenase-2 mediated diseases comprising the once a day oral administration of 5 to 125 mgs of the above mentioned compound.

The invention is also directed to the use the above mentioned compound in the manufacture of a medicament containing 5 to 125 mgs of said compound for once a day administration for the treatment of cyclooxygenase-2 mediated diseases.

DETAILED DESCRIPTION OF THE INVENTION

In one embodiment, this invention is directed to a pharmaceutical composition for the treatment of cyclooxygenase-2 mediated diseases, said composition being suitable for once a day administration, said composition comprising a cyclooxygenase-2 inhibitor characterized by high potency for the inhibition of cyclooxygenase-2, a long half-life and a high degree of specificity for inhibiting cyclooxygenase-2 in preference to cyclooxygenase-1.

In one genus, of this embodiment, this invention is directed to a pharmaceutical composition for the treatment of cyclooxygenase-2 mediated diseases, said composition being suitable for once a day oral administration, said composition comprising a cyclooxygenase-2 inhibiting compound characterized by.

(a) high potency for the inhibition of cyclooxygenase-2 as measured by the ability of a single therapeutic dose of said compound to provide relief from the post-operative pain accompanying the removal of two or three molars, said relief being statistically equal to or greater than that obtained with a single dose of 400 mg of ibuprofen;

(b) a half-life or 9 or more hours, preferably 15 hours or more and more preferably 18 hours or more; and (c) a high degree of specificity for inhibiting cyclooxygenase-2 in preference to cyclooxygenase-1 as measured by the statistical failure of a therapeutic dose of said compound to inhibit the generation of serum thromboxane B2.

One such compound is 3-phenyl-4-(4-methylsulfonyl) phenyl)-2-(5H)-furanone,

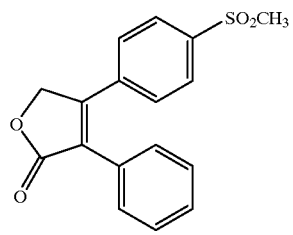

As will be appreciated by those of skill in the art, this invention is directed only to compounds which act by inhibiting cyclooxygenase-2. Thus, the characterization requirements set out above cannot be said to be met unless the mode of action of the compound is as an inhibitor of cyclooxygenase-2. For example, a central nervous system agent may relieve pain with a potency equal to or greater than ibuprofen, yet not meet the requirements set out above, because it does not act on cyclooxygenase-2. See Inflamm. Res. 45:68–74 (1996) incorporated herein by reference, which discloses an (LPS)-challenge test for clinical identification and evaluation of cyclooxygenase-2 inhibition, and thromboxane B2 levels in the blood. Equivalent tests may also be used. Compounds of the instant invention are not hepatotoxic at therapeutic doses. Moreover, compounds of the instant invention demonstrate an $ED_{30}$ in the rat paw edema assay of 0.4 mg/kg or less when measured as disclosed in WO 95/00501 and a selectivity for the inhibition of COX-2 over COX-1 of 50:1 or more measured as disclosed on WO 95/00501.

In one embodiment, this invention is directed to a pharmaceutical composition for the treatment of cyclooxygenase-2 mediated diseases, said composition being suitable for once a day oral administration, said composition comprising a 5 to 125 mg of 3-phenyl-4-(4-methylsulfonyl)phenyl)-2-(5H)-furanone, and a pharmaceutical carrier therefor.

3-Phenyl-4-(4-methylsulfonyl)phenyl)-2-(5H)-furanone, its utility and methods of making them are disclosed in U.S. Pat. No. 5,474,995, issued Dec. 12, 1995, WO 95/00501, published Jan. 5, 1995 and WO 95/18799, published Jul. 13, 1995, which are hereby incorporated by reference.

As discussed in U.S. Pat. No. 5,474,995 compounds, including 3-phenyl-4-(4-methylsulfonyl)phenyl)-2-(5H)-furanone, are useful for the relief of pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis, degenerative joint diseases (osteoarthritis), gout and ankylosing spondylitis, bursitis, burns, injuries following surgical and dental procedures. In addition, such a compound may inhibit cellular neoplastic transformations and metastic tumor growth and hence can be used in the treatment of cancer. It is also useful for the treatment of dementia including pre-senile and senile dementia, and in particular, dementia associated with Alzheimer Disease (ie Alzheimer's dementia).

The compound will also inhibit prostanoid-induced smooth muscle contraction by preventing the synthesis of contractile prostanoids and hence may be of use in the treatment of dysmenorrhea, premature labor and asthma.

By virtue of its high cyclooxygenase-2 (COX-2) inhibitory activity and/or its selectivity for inhibiting COX-2 over cyclooxygenase-1 (COX-1) the specified compound is also useful as an alternative to conventional non-steroidal anti-inflammatory drugs (NSAID'S) particularly where such NSAIDS may be contra-indicated such as in patients with peptic ulcers, gastritis, regional enteritis, ulcerative colitis, diverticulitis or with a recurrent history of gastrointestinal lesions; GI bleeding, coagulation disorders including anemia such as hypoprothrombinemia, haemophilia or other bleeding problems (including those relating to reduced or impaired platelet function); kidney disease (eg impaired renal function); those prior to surgery or taking anticoagulants; and those susceptible to NSAID induced asthma.

For the treatment of any of these cyclooxygenase mediated diseases the compound may be administered orally or by intravenous infusion.

As indicated above, pharmaceutical compositions for treating COX-2 mediated diseases as defined may optionally include one or more ingredients as listed above.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. The compositions are intended for oral use and may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc.

Other suitable formulations are set forth in U.S. Pat. No. 5,474,995. However, in view of the unique set of properties possessed by 3-phenyl-4-(4-methylsulfonyl)phenyl)-2-(5H)-furanone, including long half-life, low solubility, high potency, de minimis gastrointestinal (GI) side effects, we have found the following oral formulations to be of particular value:

Rapidisc®—In view of the above mentioned characteristics, 3-phenyl-4-(4-methylsulfonyl)phenyl)-2-(5H)-furanone is particularly well suited for a rapid dissolving sublingual formulation. For example, due to the lack of GI side-effects, the agent need not be take with a large amount of water. Suitable Rapidisc® formulations and methods of making same are disclosed in U.S. Pat. Nos. 4,305,502, 4,371,516, 4,470,202, 4,758,598, 4,754,597, 5,046,618 and 5,188,882, all of which are hereby incorporated by reference.

As mentioned in the Background section, we have found 3-phenyl-4-(4-methylsulfonyl)phenyl)-2-(5H)-furanone to possess a surprising combination of attributes. Not only are these active agents potent safe and effective at modest oral dosages of 5 to 125 mg of agent per day, but in addition these active agents possess a half-life in humans of sufficient length that a single oral dose of 5 to 125 mg of active agent per day will provide effective safe anti-inflammatory treatment over a 24 hour period. Such agents are particularly useful in the treatment of chronic indications, such as rheumatoid and osteo arthritis as well as Alzheimer's Disease.

Oral and intravenous dosage levels for agent 3-phenyl-4-(4-methylsulfonyl)phenyl)-2-(5H)-furanone are of the order of from about 5 to 125 per patient per day.

The amount of active agent that may be combined with the carrier materials to produce a single dosage form will vary depending upon the host treated and the particular mode of administration. For example, a formulation intended for the oral administration of humans may contain from 5 to 125 mg of agent compounded with an appropriate and convenient amount of carrier material which may vary from about 5 to about 95 percent of the total composition. Dosage unit forms may typically contain 5, 10, 12.5, 20, 25, 50, 75, 100 or 125 mg of active agent.

It will be understood, however, that the specific dose level for any particular patient will depend upon a variety of factors including the age, body weight, general health, sex, diet, time of administration, rate of excretion, drug combination and the type and severity of the particular disease undergoing therapy. For many patients, a dosage range of 5 to 50 or 12.5 to 25 or 25 to 75 mg per day is preferred.

For long term therapy, such as in the treatment of chronic diseases including rheumatoid arthritis, osteoarthritis or Alzheimer disease, a dosage of 5 to 50 or 12.5 to 25 mg per day is preferred. More particularly, for the treatment of osteoarthritis, a dosage of 5, 10, 12.5, 25 or 50 mg per day is preferred, whereas for the treatment of rheumatoid arthritis, 10, 12.5, 25 or 50 mg per day is preferred. For the treatment of non-chronic indications such as headache or post-operative swelling and pain, 10, 12.5, 25 or 50 mg per day is preferred.

Accordingly, in one aspect the invention is directed to a unit dose oral form which comprises from 5 to 50 or 5 to 22.5 mg of the cyclooxygenase inhibitor, for example, 12.5 or 20 mg or 12.5 to 25.

In another aspect this invention is directed to a pharmaceutical composition for the treatment of cyclooxygenase-2 mediated diseases, said composition suitable for once a day oral administration, said composition comprising a 5 to 50 or 25 to 75 mg of 3-phenyl-4-(4-methylsulfonyl)phenyl)-2-(5H)-furanone, and a pharmaceutical carried therefor.

Within this aspect there is a first genus of compositions comprising 5 to 50 mg of 3-phenyl-4-(4-methylsulfonyl)phenyl)-2-(5H)-furanone.

Within this aspect there is a second genus of compositions comprising 10 to 50 mg of 3-phenyl-4-(4-methylsulfonyl)phenyl)-2-(5H)-furanone.

Within this genus there is a class of compositions comprising 5 to 22.5 mg of 3-phenyl-4-(4-methylsulfonyl)phenyl)-2-(5H)-furanone.

Within this genus there is a class of compositions comprising 12.5 to 25 mg of 3-phenyl-4-(4-methylsulfonyl)phenyl)-2-(5H)-furanone.

Within this genus there is a class of compositions comprising 5, 10, 12.5, 25 or 50 mg of 3-phenyl-4-(4-methylsulfonyl)phenyl)-2-(5H)-furanone.

EXAMPLE 1

Wet granulated tablet composition

| Amount per tablet | Ingredient |
|---|---|
| 25 mg | COX-2 Inhibitor |
| 79.7 mg | Microcrystalline cellulose |
| 79.7 mg | Lactose monohydrate |
| 6 mg | Hydroxypropyl cellulose |
| 8 mg | Croscarmellose sodium |
| 0.6 mg | Iron oxide |
| 1 mg | Magnesium stearate |

Tablet dose strengths of between 5 and 125 mg can be accomodated by varying total tablet weight, and the ratio of the first three ingredients. Generally it is preferable to maintain a 1:1 ratio for microcrystalline cellulose: lactose monohydrate.

EXAMPLE 1a

Wet granulated tablet composition

| Amount per tablet | Ingredient |
|---|---|
| 12.5 mg | COX-2 Inhibitor |
| 86 mg | Microcrystalline cellulose |
| 86 mg | Lactose monohydrate |
| 6 mg | Hydroxypropyl cellulose |
| 8 mg | Croscarmellose sodium |
| 0.6 mg | Iron oxide |
| 1 mg | Magnesium stearate |

EXAMPLE 1b

Wet granulated tablet composition

| Amount per tablet | Ingredient |
|---|---|
| 10 mg | COX-2 Inhibitor |
| 87.2 mg | Microcrystalline cellulose |
| 87.2 mg | Lactose monohydrate |
| 6 mg | Hydroxypropyl cellulose |
| 8 mg | Croscarmellose sodium |
| 0.6 mg | Iron oxide |
| 1 mg | Magnesium stearate |

EXAMPLE 1c

Wet granulated tablet composition

| Amount per tablet | Ingredient |
|---|---|
| 5 mg | COX-2 Inhibitor |
| 89.7 mg | Microcrystalline cellulose |
| 89.7 mg | Lactose monohydrate |
| 6 mg | Hydroxypropyl cellulose |
| 8 mg | Croscarmellose sodium |
| 0.6 mg | Iron oxide |
| 1 mg | Magnesium stearate |

EXAMPLE 2

Directly compressed tablet composition

| Amount per tablet | Ingredient |
| --- | --- |
| 25 mg | COX-2 Inhibitor |
| 106.9 mg | Microcrystalline cellulose |
| 106.9 mg | Lactose anhydrate |
| 7.5 mg | Crosmellose sodium |
| 3.7 mg | Magnesium stearate |

Tablet dose strengths of between 5 and 125 mg can be accomodated by varying total tablet weight, and the ratio of the first three ingredients. Generally it is preferable to maintain a 1:1 ratio for microcrystalline cellulose: lactose monohydrate.

EXAMPLE 2a

| Directly compressed tablet composition | |
| --- | --- |
| Amount per tablet | Ingredient |
| 12.5 mg | COX-2 Inhibitor |
| 113.2 mg | Microcrystalline cellulose |
| 113.2 mg | Lactose anhydrate |
| 7.5 mg | Croscarmellose sodium |
| 3.7 mg | Magnesium stearate |

EXAMPLE 2b

| Directly compressed tablet composition | |
| --- | --- |
| Amount per tablet | Ingredient |
| 10 mg | COX-2 Inhibitor |
| 42.5 mg | Microcrystalline cellulose |
| 42.5 mg | Lactose anhydrate |
| 4 mg | Croscarmellose sodium |
| 1 mg | Magnesium stearate |

EXAMPLE 2c

| Directly compressed tablet composition | |
| --- | --- |
| Amount per tablet | Ingredient |
| 5 mg | COX-2 Inhibitor |
| 45 mg | Microcrystalline cellulose |
| 45 mg | Lactose anhydrate |
| 4 mg | Croscarmellose sodium |
| 1 mg | Magnesium stearate |

EXAMPLE 3

| Hard gelatin capsule composition | |
| --- | --- |
| Amount per capsule | Ingredient |
| 25 mg | COX-2 Inhibitor |
| 37 mg | Microcrystalline cellulose |
| 37 mg | Lactose anhydrate |
| 1 mg | Magnesium stearate |
| 1 capsule | Hard gelatin capsule |

Capsule dose strengths of between 1 and 50 mg can be accomodated by varying total fill weight, and the ratio of the first three ingredients. Generally it is preferable to maintain a 1:1 ratio for microcrystalline cellulose: lactose monohydrate.

EXAMPLE 4

| Oral solution | |
| --- | --- |
| Amount per 5 mL dose | Ingredient |
| 50 mg | COX-2 Inhibitor |
| to 5 mL with Polyethylene oxide 400 | |

Solution dose strengths of between 1 and 50 mg/5 mL can be accomodated by varying the ratio of the two ingredients.

EXAMPLE 5

| Oral suspension | |
| --- | --- |
| Amount per 5 mL dose | Ingredient |
| 101 mg | COX-2 Inhibitor |
| 150 mg | Polyvinylpyrrolidone |
| 2.5 mg | Poly oxyethylene sorbitan monolaurate |
| 10 mg | Benzoic acid |
| to 5 mL with sorbitol solution (70%) | |

Suspension dose strengths of between 1 and 50 mg/5 ml can be accomodated by varying the ratio of the first two ingredients.

EXAMPLE 6

| Intravenous infusion | |
| --- | --- |
| Amount per 200 mL dose | Ingredient |
| 1 mg | COX-2 inhibitor |
| 0.2 mg | Polyethylene oxide 400 |
| 1.8 mg | Sodium chloride |
| to 200 mL | Purified water |

STARTING MATERIALS

PREPARATION 1

3-(Phenyl)-4-(4-(methylsulfonyl)phenyl)-2-(5H)-furanone

Step 1: 2-Bromo-1-(4-(methylsulfonyl)phenyl)ethanone

A solution of 197 g of 4-(methylthio)acetophenone (ref: J. Am. Chem. Soc., 1952, 74, p. 5475) in 700 mL of MeOH and 3500 mL of $CH_2Cl_2$ was added 881 g of MMPP over a period of 30 min. After 3 h at r.t. the reaction mixture was filtered and the filtrate was washed with 2 L of saturated aqueous solution of $NaHCO_3$ and 1 L of brine. The aqueous phase was further extracted with 2 L of $CH_2Cl_2$. The combined extracts were dried over $Na_2SO_4$ concentrated to give 240 g of 4-(methylsulfonyl)acetophenone as a white solid.

To a cooled (−5° C.) solution of 174 g of 4-(methylsulfonyl)-acetophenone in 2.5 L of $CHCl_3$ was added 20 mg of $AlCl_3$, followed by a solution of 40 mL of $Br_2$ in 300 mL CHCl3. The reaction mixture was then treated with 1.5 L of $H_2O$ and the $CHCl_3$ was separated. The aqueous layer was extracted with 1 L of EtOAc. The combined organic extracts were dried over $Na_2SO_4$ and concentrated. The crude product was recystallized from 50/50 EtOAc/hexane to give 210 g of the title compound as a white solid.

Step 2: 3-(Phenyl)-4-(4-(methylsulfonyl)phenyl)-2-(5H)-furanone

To a solution of phenylacetic acid (27.4 g, 201 mmol) and 2-bromo-1-(4-(methylsulfonyl)phenyl)ethanone (Step 1) (60 g, 216 mmol, 1.075 eq.) in acetonitrile (630 mL) at 25° C. was added slowly $Et_3N$ (30.8 mL, 1.1 eq.). The mixture was stirred for 20 min. at r.t. and then cooled in an ice bath. DBU (60.1 mL, 3 eq.) was slowly added. After stirring for 20 min. in the ice bath, the reaction was complete and the mixture was acidified with 1N HCl (color changed from dark brown to yellow). Then 2.4 L of ice and $H_2O$ were added, the mixture was stirred for a few minutes, and the precipitate was filtered and rinsed with $H_2O$, giving 64 g of crude wet product. The solid was dissolved in 750 mL of $CH_2Cl_2$, dried over $MgSO_4$, filtered and 300 g of silica gel was added to the filtrate. The solvent was evaporated to near dryness (silica gel a bit sticky), the residue was applied on top of a silica gel plug in a sintered glass funnel and eluted with 10% $EtOAc/CH_2Cl_2$, giving after evaporation of the solvent and swishing in EtOAc, 36.6 g (58%) of the title compound.

Analysis: Calculated for $C_{17}H_{14}O_4S$: C, 64.95; H, 4.49; S, 10.20 Found: C, 64.63; H, 4.65; S, 10.44

PREPARATION 2
3-(Phenyl)-4-(4-(methylsulfonyl)phenyl)-2-(5H)-furanone

Into a 20 mL glass ampule are added 1 g of 2-(4-(methylsulfonyl)phenyl)phenylacetylene (J. Am. Chem. Soc., 1971, 93, p. 2979), 20 mg of $Rh_4(CO)_{12}$, 1.5 g of $Et_3N$, 10 mL of THF, and 1 mL of $H_2O$ under a nitrogen atmosphere, and the ampule is placed in a 100-mL stainless steel autoclave. The reaction system is flushed three times with CO then charged at r.t. to an initial CO pressure of 100 atm. The reaction is carried out at 100° C. for 5 h. The solution is then diluted with 50 mL of benzene and washed with brine and 1N HCl. The benzene solution is dried over $Na_2SO_4$, and concentrated. The crude products are separated by column chromatography on silica gel, eluting with 2:1 EtOAc/hexane to give the title compound and its regioisomer.

PREPARATION 3
3-(Phenyl)-4-(4-(methylsulfonyl)phenyl)-2-(5H)-furanone
Step 1: 2-trimethylsilyloxy-4-(4-(methylthio)phenyl)-3,4-dihydrofuran To a solution of 3.86 g (19 mmol) of 4-bromothioanisole in 90 mL of $Et_2O$ cooled at −78° C., is added 22 mL of a 1.7 M solution of t-BuLi in pentane (38 mmol) dropwise. The reaction mixture is stirred for 15 min at −78° C. and 3.8 g of CuI is added and the reaction mixture is allowed to warm to −40° C. over a period of 30 min. A solution of 1.7 g of 2(5H)-furanone in 10 mL of THF is added. After stirring for 1 h, 2 mL of freshly distilled TMSCl is added dropwise. The reaction mixture is then treated with 2 mL of $Et_3N$ and 50 mL of sat. $NaHCO_3$, and extracted with 100 mL of $Et_2O$. The $Et_2O$ layer is dried over $Na_2SO_4$ and concentrated to give the crude title compound which is used for the next step without further purification.

Step 2: 4-(4-(Methylthio)phenyl)-2-(5H)-furanone

To a solution of 4 g of $Pd(OAc)_2$ in 100 mL of acetonitrile is added dropwise the crude product from Step 1(5 g) under nitrogen at r.t. After 10 h at r.t., the mixture is concentrated under reduced pressure and the residue is purified by flash chromatography on silica gel eluted with 2:1 hexane/EtOAc to give the title compound.

Step 3: 3-Iodo-4-(4-(methylthio)phenyl)-2-(5H)-furanone

To a solution of 3 g of the product of Step 2 in 30 mL of pyridine is added 8.7 g of $I_2$. The mixture is stirred for 24 h and then diluted with 200 mlL of $Et_2O$, washed with 100 mL of 5N HCl and 50 mL of 5N $Na_2S_2O_3$. The $Et_2O$ layer is dried over $Na_2SO_4$ and concentrated to give the title compound.

Step 4: 3-(Phenyl)-4-(4-(methylthio)phenyl)-2-(5H)-furanone

A mixture of 4 g of the product of Step 3, 3.7 g of $PhB(OH)_2$, 0.4 g of $Ph_3As$, 0.4 g of $PdCl_2(PhCN)_2$ in 100 mL of benzene and 15 mL of 2N NaOH is refluxed for 6 h. After cooling to r.t., $Et_2O$ (200 mL) is added to the reaction mixture and the mixture is washed with 100 mL of saturated $NaHCO_3$. The organic layer is dried over $MgSO_4$ and concentrated. The residue is purified by flash chromatography on silica gel eluted with 4:1 hexane/EtOAc to give the title compound.

Step 5: 3-(Phenyl)-4-(4-(methylsulfonyl)phenyl)-2-(5H)-furanone

To a solution of 3 g of the product of Step 4 in 80 mL of 10:1 $CH_2Cl_2/MeOH$ is added 5.5 g of MMPP. The reaction mixture is stirred at r.t. for 2 h and then diluted with 100 mL of 1:1 hexane/EtOAc. After filtration and concentration, the residue is purified by flash chromatography eluted with 2:1 EtOAc/hexane to give the title product.

ABBREVIATIONS
DBU=1,8-diazabicyclo[5.4.0]undec-7-ene
$Et_3N$=triethylamine
MMPP=magnesium monoperoxyphthalate
THF=tetrahydrofuran
TMSCl=trimethylsilyl chloride

What is claimed is:

1. A method of treating a disease susceptible to treatment with an non-steroidal anti-inflammatory agent comprising:

administration orally once a day to a human patient in need of such treatment 12.5 or 25 or 50 mg of 3-phenyl-4-(4-methylsulfonyl)phenyl)-2-(5H)-furanone.

2. A method according to claim 1 for the treatment of non-chronic headache, pain or swelling.

3. A method according to claim 1 for the treatment of osteoarthritis.

4. A method according to claim 1 for the treatment of rheumatoid arthritis.

5. A method according to claim 1 for the treatment of pain.

6. A method according to claim 1 for the treatment of fever.

7. A method according to claim 1 for the treatment of dysmenorrhea.

8. A method according to claim 1 for the treatment of Alzheimer's disease.

* * * * *

UNITED STATES PATENT AND TRADEMARK OFFICE
CERTIFICATE OF CORRECTION

PATENT NO.   : 6,063,811
DATED        : May 16, 2000
INVENTOR(S)  : Bruno Hancock, Conrad Winters, Barry Gertz and Elliot Ehrich It is certified that error appears in the above-identified patent and that said Letters Patent is hereby corrected as shown below:

<u>Title page, item [19]</u>
At the top of the title page, below "United States Patent", please delete "Hancock, et al" and insert therefore -- Ehrich, et al. --.

After "[75] Inventors:", please delete "Bruno Hancock, Beaconsfield; Conrad Winters, L'Ile Bizard, both of Canada;".

Signed and Sealed this

Twenty-fifth Day of September, 2001

*Attest:*

*Attesting Officer*

NICHOLAS P. GODICI
*Acting Director of the United States Patent and Trademark Office*